US00PP36460P2

(12) United States Plant Patent
Tomomatsu et al.

(10) Patent No.: US PP36,460 P2
(45) Date of Patent: Feb. 18, 2025

(54) ***CATHARANTHUS* PLANT NAMED 'CaTU 1917'**

(50) Latin Name: *Catharanthus roseus*
Varietal Denomination: CaTU 1917

(71) Applicants: Koichi Tomomatsu, Shiga (JP); Thunya Taychasinpitak, Nonthaburii (TH); Kenichi Suzuki, Osaka (JP)

(72) Inventors: Koichi Tomomatsu, Shiga (JP); Thunya Taychasinpitak, Nonthaburii (TH); Kenichi Suzuki, Osaka (JP)

(73) Assignee: SunTory Flowers Limited, Tokyo (JP)

( * ) Notice: Subject to any disclaimer, the term of this patent is extended or adjusted under 35 U.S.C. 154(b) by 0 days.

(21) Appl. No.: 18/620,515

(22) Filed: Mar. 28, 2024

(51) Int. Cl.
*A01H 5/02* (2018.01)
*A01H 6/08* (2018.01)

(52) U.S. Cl.
USPC ..... Plt./263.1

(58) Field of Classification Search
USPC ..... Plt./263.1
CPC . A01H 5/02; A01H 5/00; A01H 6/084; A01H 6/08
See application file for complete search history.

(56) References Cited

PUBLICATIONS

Grower Talks 2023 California Spring Trials Day 2: Green Fuse & Santa Barbara Polo Club, retrieved on Jul. 17, 2024, pp. 1-20. (Year: 2023).*
MNP Suntory Soiree Cerise White Eye retrieved on Apr. 18, 2024 at https://mnpflowers.com/product/soiree-cerise-white-eye/, 5 pp. (Year: 2024).*
Suntory Flowers 2024 Catalog, retrieved on Jul. 17, 2024 at https://online.flippingbook.com/view/1047998325/, pp. 1-3, 22-23. (Year: 2024).*
Thursd. MNP/Suntory's New Stand, New Position, and New Business Opportunities at IBP 2024, retrieved on Jul. 18, 2024 at https://thursd.com/articles/mnp-suntory-ipm-essen-2024, 10 pp. (Year: 2024).*

* cited by examiner

*Primary Examiner* — June Hwu
(74) *Attorney, Agent, or Firm* — C. Anne Whealy

(57) ABSTRACT

A new and distinct cultivar of *Catharanthus* plant named 'CaTU 1917', characterized by its compact, upright and uniformly mounding plant habit; vigorous growth habit; freely basal branching habit; freely flowering habit; long flowering period; relatively small star-shaped dark red-colored flowers with pale yellow-colored centers; and good garden performance.

2 Drawing Sheets

Figure 1:
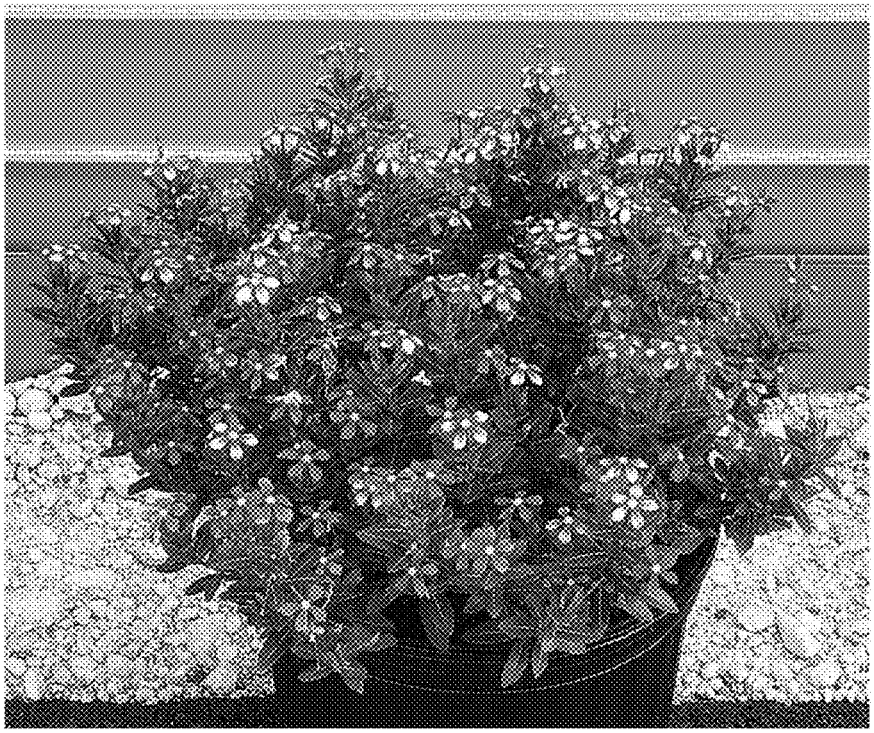

Botanical designation: *Catharanthus roseus.*
Cultivar denomination: 'CaTU 1917'.

STATEMENT REGARDING PRIOR DISCLOSURES BY THE INVENTORS/APPLICANTS & ASSIGNEE

The Inventors/Applicants and Assignee, Suntory Flowers Limited of Tokyo, Japan, assert that no publications nor advertisements relating to sales, offers for sale or public distribution occurred more than one year prior to the effective filing date of this application. Any information about the claimed plant would have been obtained from a direct or indirect disclosure from the Inventors/Applicants and/or the Assignee. Inventors/Applicants and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct *Catharanthus* plant, botanically known as *Catharanthus roseus* and hereinafter referred to by the cultivar name 'CaTU 1917'.

The new *Catharanthus* plant is a product of a planned breeding program conducted by the Inventors in Higashiomi, Shiga, Japan. The objective of the breeding program is to develop new compact and freely branching *Catharanthus* plants with numerous small attractive flowers.

The new *Catharanthus* plant originated from a self-pollination in Higashiomi, Shiga, Japan in June 2018 of a proprietary selection of *Catharanthus roseus* identified as code designation Tu19, not patented. The new *Catharanthus* plant was discovered and selected by the Inventors as a single flowering plant from within the progeny of the stated self-pollination in a controlled greenhouse environment in Higashiomi, Shiga, Japan in February 2019.

Asexual reproduction of the new *Catharanthus* plant by vegetative tip cuttings in a controlled greenhouse environment in Higashiomi, Shiga, Japan since December 2019, has shown that the unique features of this new *Catharanthus* plant are stable and reproduced true to type in successive generations.

SUMMARY OF THE INVENTION

Plants of the new *Catharanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'CaTU 1917'. These characteristics in combination distinguish 'CaTU 1917' as a new and distinct *Catharanthus* plant:

1. Compact, upright and uniformly mounding plant habit.
2. Vigorous growth habit.
3. Freely basal branching habit.
4. Freely flowering habit.
5. Long flowering period.
6. Relatively small star-shaped dark red-colored flowers with pale yellow-colored centers.
7. Good garden performance.

Plants of the new *Catharanthus* can be compared to plants of the parent selection. Plants of the new *Catharanthus* differ primarily from plants of the parent selection in flower size as plants of the new *Catharanthus* have smaller flowers than plants of the parent selection. In addition, flower petals of plants of the new *Catharanthus* are narrowly elliptic to oblanceolate in shape whereas flower petals of plants of the parent selection are broadly obovate to transversely elliptic in shape.

Plants of the new *Catharanthus* can be compared to plants of the *Catharanthus roseus* 'Suncath 132', disclosed in U.S. Plant Pat. No. 33,809. In side-by-side comparisons, plants of the new *Catharanthus* differ from plants of 'Suncath 132' in the following characteristics:

1. Plants of the new *Catharanthus* are more upright than plants of 'Suncath 132'.
2. Plants of the new *Catharanthus* have smaller flowers than plants of 'Suncath 132'.
3. Plants of the new *Catharanthus* and 'Suncath 132' differ in flower color as plants of the new *Catharanthus* have dark red-colored flowers whereas plants of 'Suncath 132' have purplish red-colored flowers.
4. Flowers of plants of the new *Catharanthus* have a smaller "eye zone" than flowers of plants of 'Suncath 132'.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph on the first sheet (FIG. 1) is a side perspective view of a typical flowering plant of 'CaTU 1917' grown in a container.

Figure 2:
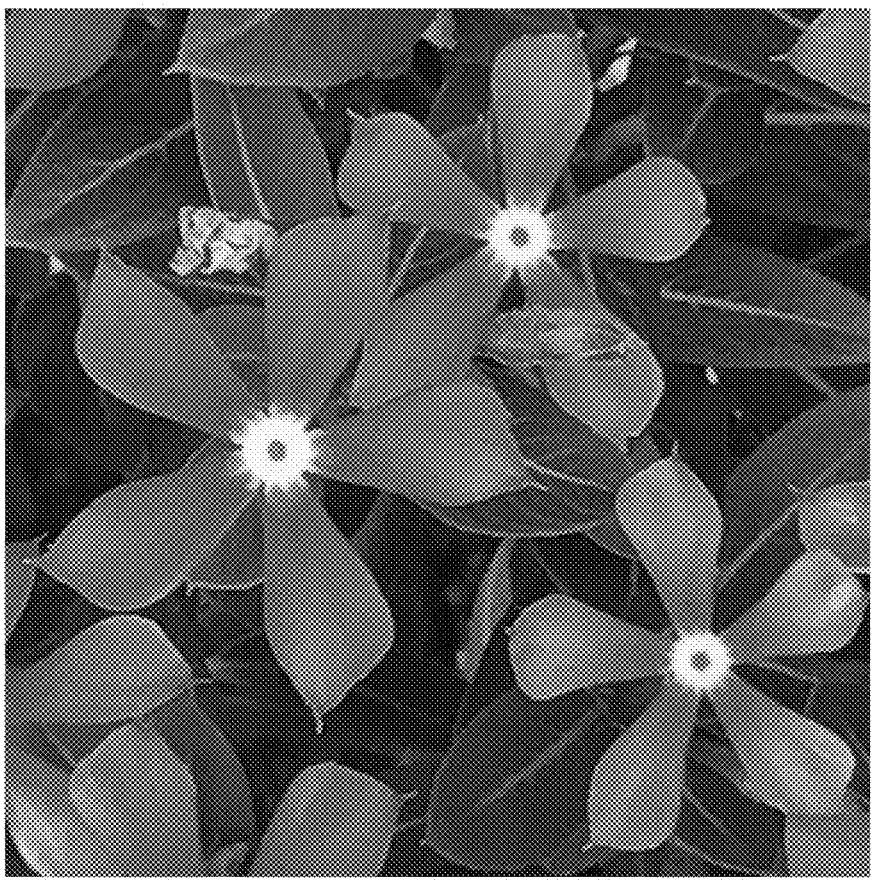

The photograph on the second sheet (FIG. 2) is a close-up view of a typical flowering plant of 'CaTU 1917'.

DETAILED BOTANICAL DESCRIPTION

The aforementioned photographs and following observations, measurements and values describe plants grown during the summer in 24-cm containers in an outdoor nursery in Higashiomi, Shiga, Japan and under cultural practices typical of commercial production. During the production of the plants, day temperatures averaged 25° C. and night temperatures averaged 15° C. Plants were four months old when the photographs and the description were taken. In the following description, color references are made to The Royal Horticultural Society Colour Chart, 2015 Edition, except where general terms of ordinary dictionary significance are used.

Botanical classification: *Catharanthus roseus* 'CaTU 1917'.

Parentage:

*Female, or seed, parent.*—Proprietary selection of *Catharanthus roseus* identified as code designation Tu19, not patented.

*Male, or pollen, parent.*—Proprietary selection of *Catharanthus roseus* identified as code designation Tu19, not patented.

Propagation:

*Type.*—By vegetative tip cuttings.

*Time to initiate roots, summer.*—About two weeks at temperatures about 30° C.

*Time to initiate roots, winter.*—About three weeks at temperatures about 25° C.

*Time to produce a rooted young plant, summer.*—About five weeks at temperatures about 30° C.

*Time to produce a rooted young plant, winter.*—About six weeks at temperatures about 25° C.

*Root description.*—Fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Compact, upright and uniformly mounding plant habit; freely basal branching habit, about seven basal branches each with about 14 secondary branches developing per plant; vigorous growth habit.

*Plant height.*—About 29 cm.

*Plant diameter.*—About 40 cm.

Lateral branch description:

*Length.*—About 19 cm.

*Diameter.*—About 3.1 mm.

*Internode length.*—About 1.3 cm.

*Strength.*—Strong.

*Aspect.*—Mostly upright.

*Texture.*—Sparsely pubescent.

*Color.*—Close to 147C; if present, anthocyanin intensity is strong.

Leaf description:

*Arrangement.*—Opposite, simple.

*Length.*—About 2.9 cm.

*Width.*—About 1.1 cm.

*Shape.*—Elliptic.

*Apex.*—Acute.

*Base.*—Obtuse.

*Margin.*—Entire.

*Texture, upper and lower surfaces.*—Sparsely pubescent.

*Venation pattern.*—Pinnate; reticulate.

*Color.*—Developing leaves, upper surface: Close to NN137B. Developing leaves, lower surface: Close to NN137C. Fully expanded leaves, upper surface: Close to NN137B; venation, close to 138B. Fully expanded leaves, lower surface: Close to 137C; venation, close to 138C.

*Petioles*.—Length: About 3.3 mm. Diameter: About 1.7 mm. Texture, upper and lower surfaces: Sparsely pubescent. Color, upper and lower surfaces: Close to 138B.

Flower description:

*Flower arrangement and habit*.—Single star-shaped salverform flowers arising from upper leaf axils; freely flowering habit with about five flowers per lateral branch and about 250 flowers developing during the flowering season; flowers face mostly upright.

*Fragrance*.—None detected.

*Flowering habit*.—Plants begin flowering about two to three weeks after planting; long flowering period, in the garden, plants flower continuously from the early summer to late autumn in Japan.

*Flower longevity*.—Individual flowers last about two to three days on the plant; flowers not persistent.

*Flower buds*.—Length: About 2.6 cm. Diameter: About 2.5 mm. Shape: Ovoid to cylindrical. Color: Distally, close to 59C, and towards the base, close to 182C.

*Flower diameter*.—About 1.9 cm.

*Flower length* (*depth*).—About 2.6 cm.

*Tube length*.—About 2.3 cm.

*Tube diameter, proximally*.—About 1.1 mm.

*Tube diameter, distally*.—About 2.2 mm.

*Corolla*.—Arrangement: Five petals in a single whorl fused at the base into a tube; petals free. Petal length from throat: About 8.8 mm. Petal width: About 5.5 mm. Petal eye zone diameter: About 2.5 mm. Petal shape: Narrowly elliptic to oblanceolate. Petal apex: Cuspidate. Petal base: Fused to corolla tube. Petal margin: Entire; not undulate to slightly undulate. Petal texture, upper and lower surfaces: Smooth, glabrous. Throat texture: Smooth, glabrous. Tube texture: Pubescent. Color: Petal, when opening and fully opened, upper surface: Close to 53C; color fading to white, close to NN155D with subsequent development, color fading first at the apex and then fading gradually towards the throat; eye zone, close to 8D. Petal, when opening and fully opened, lower surface: Close to 53D; towards the tube, close to 56A. Throat: Close to 146B to 146D. Tube: Close to 146C and 166D.

*Calyx*.—Arrangement: Star-shaped tubular calyx with five sepals fused towards the base. Sepal length: About 2 mm. Sepal width: About 1 mm. Sepal shape: Lanceolate. Sepal apex: Acuminate. Sepal margin: Entire. Sepal texture, upper and lower surfaces: Sparsely pubescent. Color, upper and lower surfaces: Close to 144A.

*Peduncles*.—Length: About 1.4 mm. Diameter: About 1.2 mm. Angle: Upright to outwardly. Strength: Strong. Texture: Sparsely pubescent. Color: Close to 144B.

*Reproductive organs*.—Stamens: Quantity per flower: Five; filaments fused to the corolla tube. Anther size: About 0.7 mm by 1.2 mm. Anther shape: Narrowly elliptic. Anther color: Close to 8C. Pollen amount: Scarce. Pollen color: Close to 8D. Pistils: Quantity per flower: One. Pistil length: About 2 cm. Style color: Close to 144C. Stigma shape: Globose. Stigma color: Close to 144B. Ovary color: Close to 144B. Seeds and fruits: To date, seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen & pest resistance: To date, plants of the new *Catharanthus* have not been observed to be resistant to pathogens and pests common to *Catharanthus* plants.

It is claimed:

1. A new and distinct *Catharanthus* plant named 'CaTU 1917' as herein illustrated and described.

* * * * *